US009877863B2

(12) United States Patent
Gammons et al.

(10) Patent No.: US 9,877,863 B2
(45) Date of Patent: Jan. 30, 2018

(54) AGITATOR FOR SURGICAL SLUSH MACHINE

(71) Applicant: Adroit Medical Systems, Inc, Loudon, TN (US)

(72) Inventors: Scott Gammons, Loudon, TN (US); Clifford E. Gammons, Loudon, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 666 days.

(21) Appl. No.: 14/175,201

(22) Filed: Feb. 7, 2014

(65) Prior Publication Data

US 2014/0226434 A1 Aug. 14, 2014

Related U.S. Application Data

(60) Provisional application No. 61/763,149, filed on Feb. 11, 2013.

(51) Int. Cl.
*A61F 7/00* (2006.01)
*A61B 46/10* (2016.01)

(52) U.S. Cl.
CPC ............. *A61F 7/00* (2013.01); *A61B 46/10* (2016.02); *A61F 2007/0063* (2013.01)

(58) Field of Classification Search
CPC ....... A61B 19/08; A61B 19/088; A61B 46/10; A61F 7/00; A61F 2007/0063
USPC ............................................................ 62/68
See application file for complete search history.

(56) References Cited

U.S. PATENT DOCUMENTS

| 5,331,820 A | 7/1994 | Faries, Jr. et al. |
| 5,457,962 A | 10/1995 | Faries, Jr. et al. |
| 5,502,980 A | 4/1996 | Faries, Jr. et al. |
| 5,857,467 A | 1/1999 | Faries, Jr. et al. |
| 6,003,328 A | 12/1999 | Faries, Jr. et al. |
| 7,350,373 B1 * | 4/2008 | Faries, Jr. .............. A61B 46/10 128/849 |

* cited by examiner

*Primary Examiner* — Tony G Soohoo
*Assistant Examiner* — Anshu Bhatia
(74) *Attorney, Agent, or Firm* — Knox Patents; Thomas A. Kulaga

(57) ABSTRACT

Apparatus for connecting a sterile drape to an actuator of a surgical slush machine. The apparatus is an agitator that includes a support member and a latch. The sterile drape is attached to one surface of the support member and the latch extends from the opposite surface of the support member. The support member is configured to flex and bend when the agitator is operated by the actuator and the drape contains a solution to be made into slush. In one embodiment the support member has paddles extending from a central position. In another embodiment the support member is a disk that has an area of weakness that allows the support member to flex and bend. In one such embodiment the area of weakness is an annular section of reduced thickness.

20 Claims, 7 Drawing Sheets

AGITATOR FOR SURGICAL SLUSH MACHINE

CROSS-REFERENCE TO RELATED APPLICATIONS

This application claims the benefit of U.S. Provisional Application No. 61/763,149, filed Feb. 11, 2013, which is herein incorporated by reference.

STATEMENT REGARDING FEDERALLY SPONSORED RESEARCH OR DEVELOPMENT

Not Applicable

BACKGROUND

1. Field of Invention

This invention pertains to a drape support or agitator for making surgical slush. More particularly, this invention pertains to a drape support mechanism or agitator attached to a drape and configured to removably attach to a surgical slush machine.

2. Description of the Related Art

The medical profession performs transplants and other surgeries in which a sterile slush solution is used. The slush is made by lowing the temperature of a saline solution in a refrigerated device that typically includes means for dislodging the congealed sterile slush solution from the sides of a slush basin. One such device is disclosed in U.S. Pat. No. 5,457,962, issued to Faries, Jr., et al., on Oct. 17, 1995, titled "Sterile drape for use in making surgical slush." The '962 patent discloses a machine used for producing and collecting sterile surgical slush. The machine includes a disk 19 with an attached sterile drape 17 that is used in a refrigerated basin 11. The disk 19 is moved repeatedly up and down and slush forms on the drape 17 adjacent the side walls and is prevented from solidifying into ice by the reciprocating movement of the disk 19. U.S. Pat. No. 5,331,820, issued to Faries, Jr., et al., on Jul. 26, 1994, titled "Method and apparatus for forming and collecting surgical slush," is the parent patent of the '962 patent.

The '962 and '980 patents identify the typical requirements for a disk 19 and attached sterile drape 17. In particular, the sterile drape material must be impervious to the solution used to make the slush and must remain flexible at the temperature used to make the slush. The drape material must also have sufficient tensile strength to resist tearing and puncturing during use. It is desirable for the material of the sterile drape to be such that ice does not readily adhere to it during slush formation. Typical drape materials disclosed in these patents include polyurethane, polyvinylchloride, thermoplastic olefins, polyethylene, polypropylene, copolymers of propylene, and polyethylene.

The '962 patent requires that the reciprocating disk 19 be "sufficiently rigid to support the pile of surgical slush without bending, flexing or breaking." Typical disk materials disclosed in these patents include polycarbonate, acronitrile-butadiene-styrene copolymer, polymethylmethacrylate, rigid polyvinylchloride, rigid polyurethane, nylon, polyethylene, polystyrene, and other rigid thermoplastics capable of being machined, thermoformed, or injection molded to the desired shape.

BRIEF SUMMARY

According to various embodiments of the present invention, a drape support mechanism or agitator for a surgical slush machine is provided. The drape support mechanism or agitator includes a support member and a latch. The drape support member provides a mechanical connection between the latch and the drape. The drape support member is attachable to the sterile drape. The agitator and drape fit inside a basin in the surgical slush machine. The latch removeably connects to the actuator, or agitator disc, in the basin of the surgical slush machine. The actuator causes the latch to move in concert with the actuator. The moving latch causes the drape support member to move, thereby agitating a slush solution contained in the drape. The portion of the drape that conforms to the shape of the basin contains a surgical slush solution.

In one embodiment, the support member of the drape support, or agitator, includes a group of paddles spaced around and extending from the central latch. In various such embodiments, the support members are flexible such that the drape support flexes and bends as the drape support agitates the slush in the basin. In this way the drape support flexes and bends so as to induce random motions to the slush solution contained in the drape. In one such embodiment, the support members have holes or slots or windows in the neck area such that the paddle heads move relative to the latch portion of the agitator. In another such embodiment, the neck area of the paddles are configured to be flexible such that they bend under load, yet have sufficient strength to support a fully loaded drape during agitation of the slush without breaking.

In another embodiment the drape support, or agitator, includes a disk with the latch attached to the center. In one embodiment, the disk is substantially rigid and supports the slush in the drape with little to no flexing or bending. In one such embodiment the drape support includes a disk with a region of weakness. The region of weakness, in one such embodiment, is an annular ring in the disk that has a thickness less than the adjacent areas of the disk. In this way the disk flexes and bends so as to induce random motions to the slush solution contained in the drape.

In one embodiment, the latch has a pair of opposed prongs. The prongs each have a sidewall and a keeper. The slush machine actuator slides between the sidewalls in a direction parallel to the drape support. The sidewalls grip the actuator between the prongs. The keeper holds the actuator captive in the space between the keeper and the rest of the agitator. In one such embodiment, the prongs include protrusions on the inside that contact a surface of the actuator and bias the actuator against the opposite surface.

In another embodiment, the latch has a plurality of opposed prongs, each with a sidewall and a ledge. The slush machine actuator slides between the sidewalls in a direction axial to the agitator. The ledges grip the actuator and hold the actuator against the bottom surface of the latch.

In another embodiment, the latch has a single sidewall that is a partial cylinder. The actuator engages the partial cylinder and is gripped thereby. The latch has a keeper that that holds the actuator captive in the space between the keeper and the rest of the drape support.

BRIEF DESCRIPTION OF THE SEVERAL VIEWS OF THE DRAWINGS

The above-mentioned features will become more clearly understood from the following detailed description read together with the drawings in which.

DETAILED DESCRIPTION

Apparatus for attaching and securing a sterile drape to a surgical slush machine agitator disc, or actuator, is disclosed. The drape support or agitator is generally indicated as 102, with particular embodiments and variations shown in the figures and described below having an alphabetic suffix, for example, 102-A, 102-B, etc.

Figure 1:
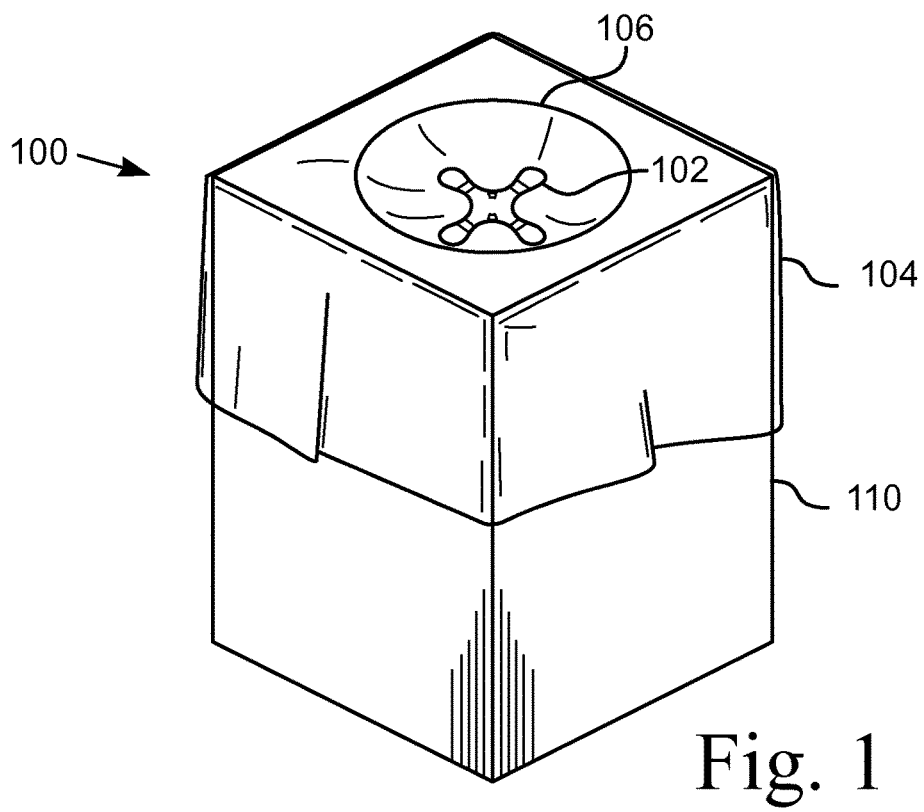
FIG. 1 is a perspective view of a surgical slush machine with a drape assembly.

FIG. 1 illustrates a perspective view of a surgical slush machine 110 with a drape assembly 100. The surgical slush machine 110 is a machine that includes a basin 106 that is refrigerated. The surgical slush machine 110 may include controls and/or a warming tray (not illustrated) to assist medical workers in creating and maintaining the slush. Generally, the slush machine 110 includes an actuator 310 that oscillates or reciprocates inside the basin 106.

The drape assembly 100 includes a drape 104 and a drape support assembly or agitator 102. The outer surface of the drape 104 is sterile and the opposite surface of the drape 104 is attached to the center top portion of the drape support assembly 102. In one embodiment, the drape 104 is a clear sheet of flexible polyurethane that is thin, approximately 1 to 10 mils, and the drape support assembly 102 is formed of polycarbonate that is approximately 1/32 to 1/16 inch thick (approximately 30 to 60 mils). The drape 104 is sized to extend from the drape support assembly 102, generally conform to the sides of the basin 106, and cover the top and extend partly down the sides of the surgical slush machine 110.

Figure 2:
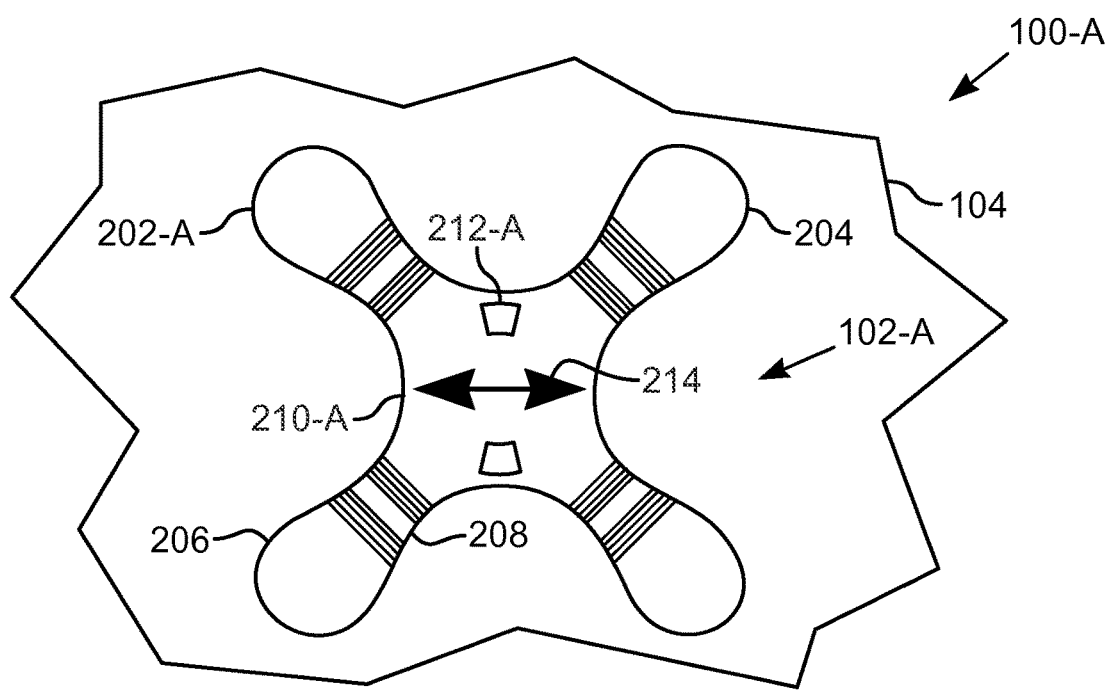
FIG. 2 is a partial view of one embodiment of a drape assembly.

FIG. 2 illustrates a partial view of one embodiment of a drape assembly 100-A. The drape assembly 100-A includes a drape support 102-A and a drape 104, which is shown partially. The drape support 102-A is attached to the drape 104, such was by welding or an adhesive. In one embodiment, drape 104 is attached to central portion of the drape support 102-A. The side of the drape 104 opposite the side where the drape support 102-A is attached is sterile so that the slush in the surgical slush machine is not contaminated by the drape 104.

The drape support 102-A includes a support member 202-A and a latch 210-A. The support member 202-A includes paddles 204 extending outward from the center of the drape support 102-A with a flower-like configuration. The illustrated drape support 102-A has four paddles 204. The paddles 204 each have a paddle head 206 and a paddle connector or neck 208 that attaches the paddle head 206 to the center portion of the drape support 102-A that includes the latch 210-A. In one embodiment, the configuration of the paddles 204 is such that the paddles 204 flex and bend as the latch 210-A oscillates vertically when used in a slush basin 106. In other embodiments the number of paddles 204 varies and/or the length between the latch 210-A and the tip of the paddle head 206 varies between the illustrated long length to a shorter length, that is a length defined by a short paddle neck 208.

The latch 210-A is positioned in the center for the support member 202-A. The latch 210-A includes a pair of opposed prongs 212-A that extend away from the rest of the drape support 102-A. The latch 210-A engages the actuator 310 of the slush machine 110. The drape support 102-A is moved in either direction 214 to move the latch 210-A into position around the actuator 310.

Figure 3:
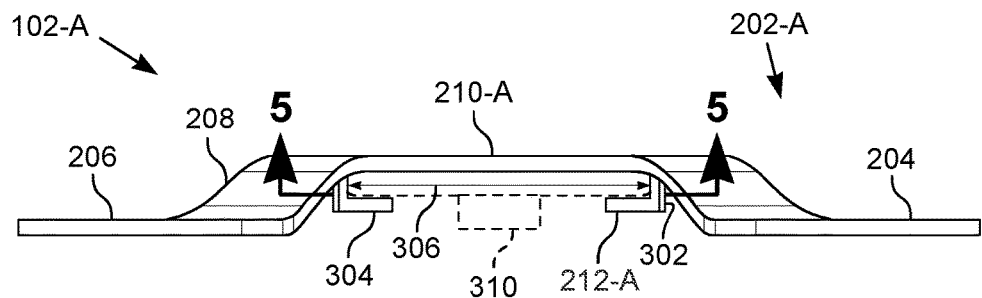
FIG. 3 is a side view of the drape support of FIG. 2 looking between a pair of paddles.
Figure 4:
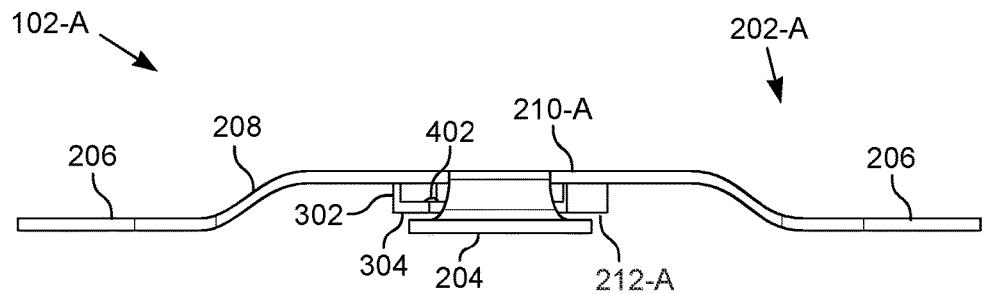
FIG. 4 is a side view of the drape support of FIG. 2 looking into one of the paddles.
Figure 5:
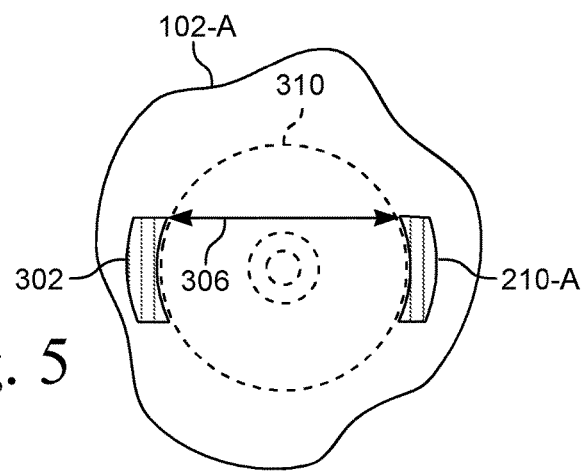
FIG. 5 is a cross-sectional view of one embodiment of the latch with an actuator, shown in phantom, in the latch.

FIG. 3 illustrates a side view of the drape support, or agitator, 102-A of FIG. 2 looking between a pair of paddles 204. FIG. 4 illustrates a side view of the drape support assembly of FIG. 2 looking into one of the paddles 204. FIG. 5 illustrates a cross-sectional view of one embodiment of the latch 210-A with an actuator 310, shown in phantom, in the latch 210-A.

The support member 202-A includes a paddle 204 that has a paddle head 206 that drops down. The neck 208 is curved to provide the transition from the level of the drape support 102-A proximate the latch 210-A to the lower level of the paddle head 206. When the drape support 102-A is positioned in the basin 106, the paddle heads 206 are configured to be proximate the inside lower surface of the basin 106.

The configuration of the paddles 204 is such that the paddles 204 flex and bend as the latch 210-A oscillates vertically in concert with the motion of the actuator 310 of the slush machine 110. The paddle connectors, or necks, 208 have a pre-formed drop such that when the drape assembly 100-A is positioned in the slush basin 106, the paddles 204 and the attached drape 104 are close to the bottom of the slush basin. In this way the volume of slush contained by the surgical slush drape 100 more closely matches the volume of the slush basin and the volume contained by the drape 104 is maximized.

The latch 210-A receives a slush basin actuator 310 when the drape support 102-A moves in a direction 214 parallel relative to the slush basin actuator 310. The slush basin actuator 310 is a metal disc about 2 inches in diameter and 1/4 inch thick. The actuator 310 reciprocates or oscillates up and down inside the basin 106, moving the drape support 102 and, consequently, a portion of the drape 104 to prevent the slush from freezing solid in the slush basin 106.

The latch 210-A has two prongs 212-A extending downward from the drape support 102-A. Each prong 212-A has a sidewall 302 and a tab or keeper 304. The sidewalls 302 have a curved inner surface that has a radius substantially equal to or slightly larger than the radius of the actuator 310. The sidewalls 302 have an inside diameter sized to accommodate the slush basin actuator 310. The latch 210-A has an opening 306 that has a width that is slightly less than the diameter of the actuator 310 such that when the drape support 102-A is moved in the direction 214 relative to the actuator 310, the latch 210-A receives the actuator 310 and holds the actuator 310 captive within the latch 210-A. The sidewalls 302 are resilient such that when the latch 210-A engages the actuator 310 the sidewalls 302 deform to allow the actuator 310 to move within the latch 210-A and be retained between the sidewalls 302.

Attached to each sidewall 302 is a keeper 304. Each keeper 304 extends toward the opposite sidewall 302 and is parallel to the base of the latch 210-A. The gap between each keeper 304 and the base of the latch 210-A is sufficient to accommodate the thickness of the actuator 310. In one embodiment, the inside surface of each keeper 304 has a raised ridge or bump 402 that engages the lower surface of the actuator 310 and biases the actuator 310 against the base of the latch 210-A. The keepers 304 hold the actuator 310 captive within the latch 100-A as the actuator 310 moves vertically during agitation.

Figure 6:
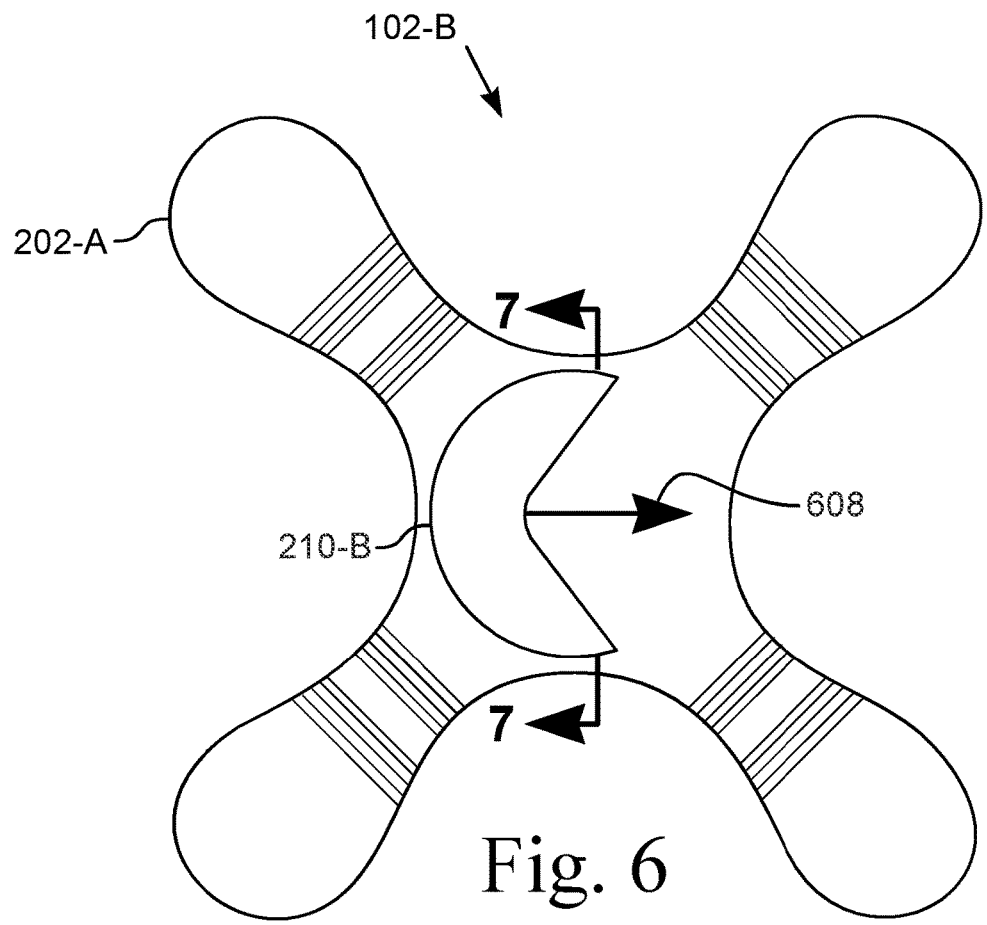
FIG. 6 is a bottom view of a second embodiment of a drape support that includes a second embodiment of a latch.
Figure 7:
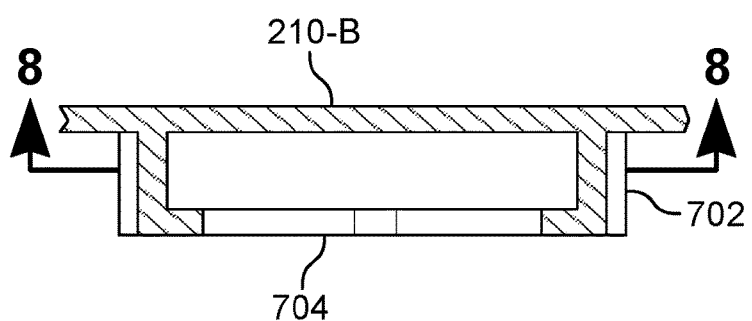
FIG. 7 is a partial cross-sectional view of the second embodiment of the latch.
Figure 8:
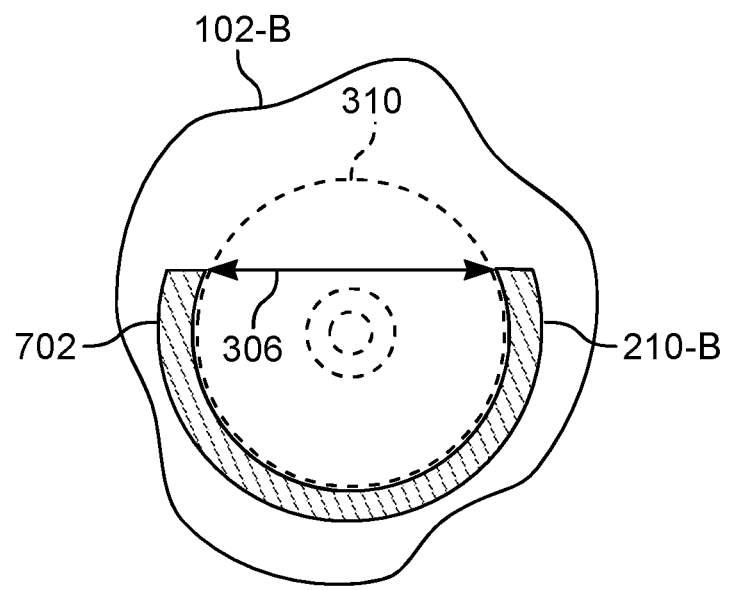
FIG. 8 is another partial cross-sectional view of the second embodiment of the latch with an actuator, shown in phantom, in the latch.

FIG. 6 illustrates a bottom view of a second embodiment of a drape support assembly 102-B that includes a second embodiment of a latch 210-B. FIG. 7 illustrates a partial cross-sectional view of the second embodiment of the latch 210-B. FIG. 8 illustrates another partial cross-sectional view of the second embodiment of the latch 210-B. The drape support 102-B includes a latch 210-B that has a sidewall 702 and a plate or keeper 704.

The sidewall 702 is a partial cylinder with an inside diameter sized to accommodate the slush basin actuator 310. The opening 306 in the sidewall 602 is slightly less than the diameter of the actuator 310 such that when the drape support 102-B is moved in the direction 608 relative to the actuator 310, the latch 110-B receives the actuator 310 and holds the actuator 310 captive within the latch 210-B. The plate 704 holds the actuator 310 captive within the latch 210-B as the actuator 310 moves vertically during agitation.

A plate, or keeper, 704 is spaced from the bottom surface of the drape support 102-B with a gap sufficient to accommodate the disk of the actuator 310. The plate 704 is notched to accommodate the shaft connection to the actuator 310. In the illustrated embodiment the plate 704 has a V-shaped notched with a rounded vertex.

Figure 9:
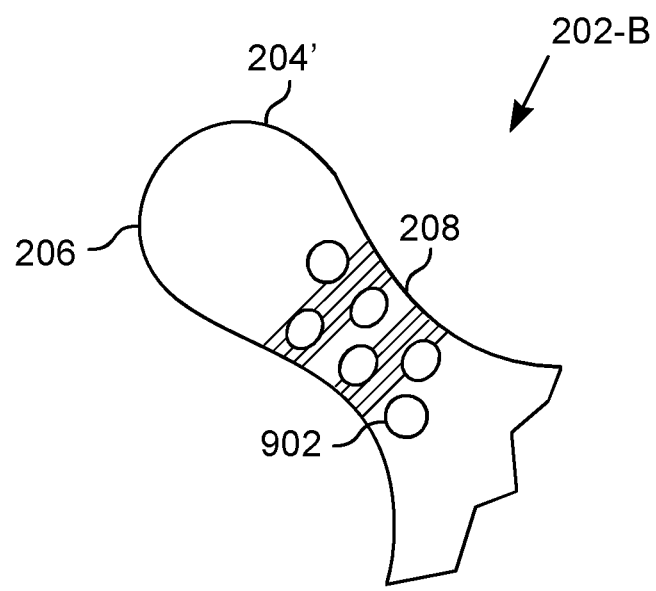
FIG. 9 is a partial view of another embodiment of a paddle.

FIG. 9 illustrates a partial view of another embodiment of a paddle 204'. In one embodiment, the drape support 102-A, 102-B is flexible or non-rigid. That is, the paddles 204, 204' have a region or area of weakness that allows the paddles 204, 204' to flex and move relative to the center portion of the drape support 102-A, 102-B and to each other. The region or area of weakness allows the paddle heads 206 to move relative to the center of the drape support 102-A, 102-B. Several factors, individually or in combination, contribute to the flexibility and bendability of the region or area of weakness. One factor is the material used for the drape support 102-A, 102-B. One such material is a polycarbonate that is rigid enough to support the weight of the slush as the drape support 102-A, 102-B agitates the slush solution in the slush basin 106, and the material bends and flexes enough under load so that there is relative motion between the paddle heads 206 and the center of the drape support 102-A, 102-B.

Another factor is the construction of the paddles 204, for example the thinness and/or width of the neck 208 between the paddle head 206 and the center of the drape support 102-A, 102-B. FIG. 9 also shows one embodiment of the paddles 204' that includes a group of holes 902 in its neck 208. In the illustrated embodiment, each of the paddles 204' includes a group of holes 902 that weaken the neck 208 of the support member 202-B where the paddle heads 206 connect to the center portion of the drape support 102-A, 102-B. The holes 902 increase the flexibility of the paddles 204' and allows the paddles 204' to flex and bend as the drape support 102-A, 102-B moves to agitate the slush in the slush basin. In various such embodiments, the holes 902 are round, such as illustrated, slotted, formed as windows, and/or have a honeycomb configuration.

Another embodiment that increases the flexibility of the drape supports 102-A, 102-B includes making the neck 208 of the paddles 204' between the paddle heads 206 and the center portion of the drape support 102-A, 102-B with a configuration that resists breakage but allows flexibility, for example, by narrowing the neck and/or molding in support ribs or structures on a surface of the paddles 204'.

Figure 10:
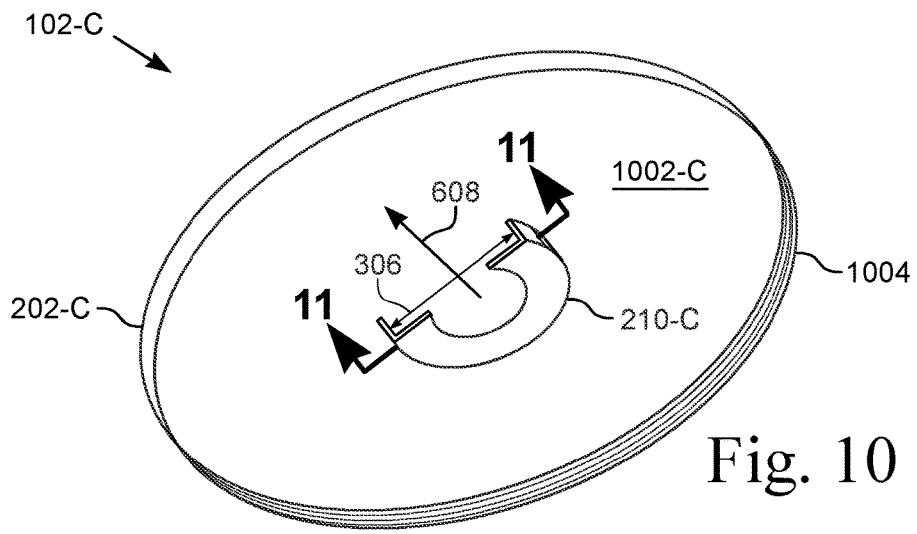
FIG. 10 is a perspective view of a third embodiment of a drape support.
Figure 11:
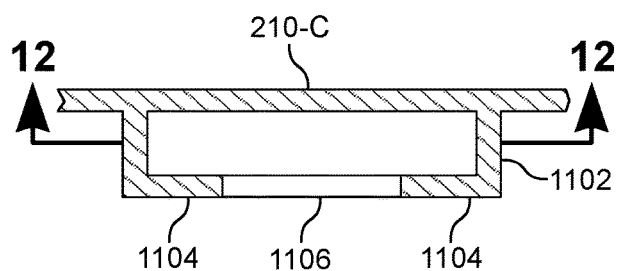
FIG. 11 is a partial cross-sectional view of a third embodiment of the latch.
Figure 12:
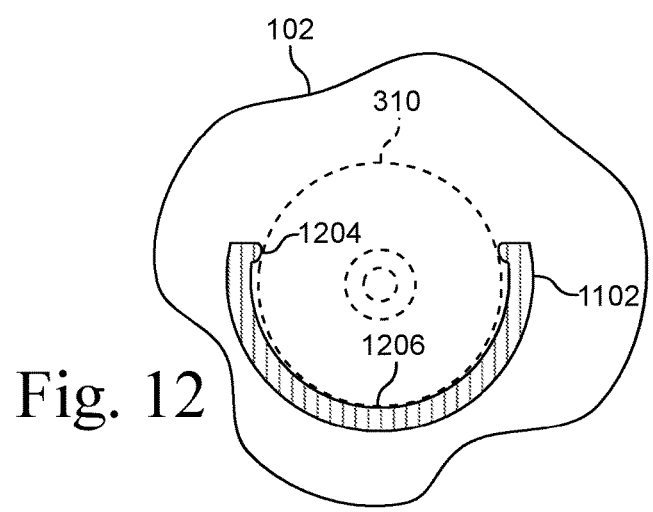
FIG. 12 is another partial cross-sectional view of the third embodiment of the latch with an actuator, shown in phantom, in the latch.

FIG. 10 illustrates a perspective view of a third embodiment of a drape support 102-C. FIG. 11 illustrates a partial cross-sectional view of a third embodiment of the latch 210-C. FIG. 12 illustrates another partial cross-sectional view of the third embodiment of the latch 210-C. The third embodiment of the drape support 102-C includes a support member 202-C and a latch 210-C.

The support member 202-C has a disk-shape. The support member 202-C includes a plate 1002-C and a rim 1004 that projects downward in the same direction that the latch 210-C projects from the plate 1002-C. The latch 210-C is positioned in the center of the drape support 202-C.

The illustrated embodiment of the latch 210-C has a sidewall 1102 that is a partial cylinder. A plate, or keeper, 1104 is spaced from the bottom surface of the drape support 102-C with a gap sufficient to accommodate the disk of the actuator 310. The plate 1104 includes a central opening 1106 that is dimensioned to accommodate the shaft connection to the actuator 310.

The sidewall 1102 of the latch 210-C has an opening with a width 306 that is slightly less than the diameter of the actuator 310 such that when the drape support 102-C is moved in the direction 608 relative to the actuator 310, the latch 210-C receives the actuator 310 and holds the actuator 310 captive within the latch 210-C. Inside the opening 306 of the sidewall 1102 at each inside edge is a protrusion 1204. The protrusions 1204 are raised bumps or ridges that extend inward from the sidewall 1102. The sidewall 1102 is resilient such that when the latch 210-C engages the actuator 310 the sidewall 1102 deforms to allow the actuator 310 to move within the latch 210-C and be retained between the sidewall 1102. When the actuator 310 is held captive by the sidewall 1102, the protrusions 1204 and a point 1206 located on the back inside wall of the sidewall 1102 contact points on the circumference of the actuator 310, thereby securing the actuator 310 to the sidewall 1102 and to the drape support 102-C.

Figure 13:
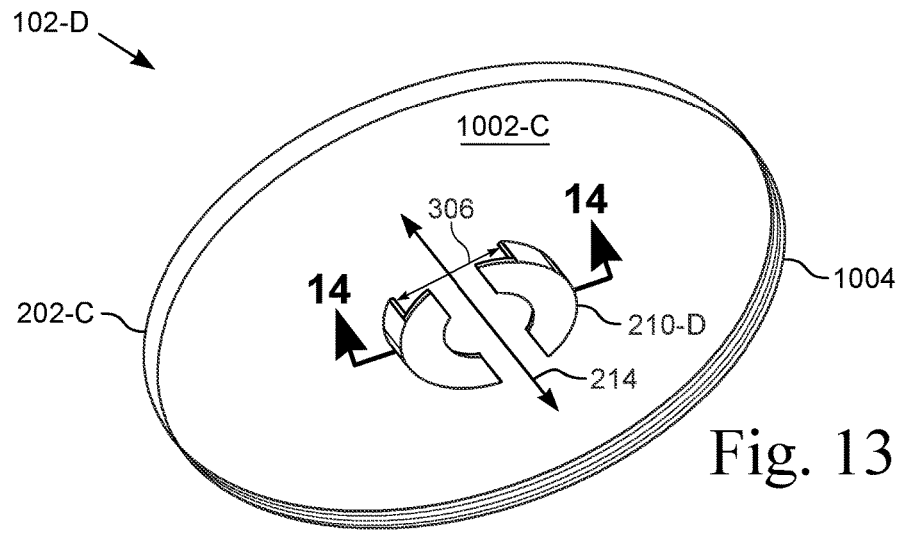
FIG. 13 is a perspective view of a fourth embodiment of a drape support.
Figure 14:
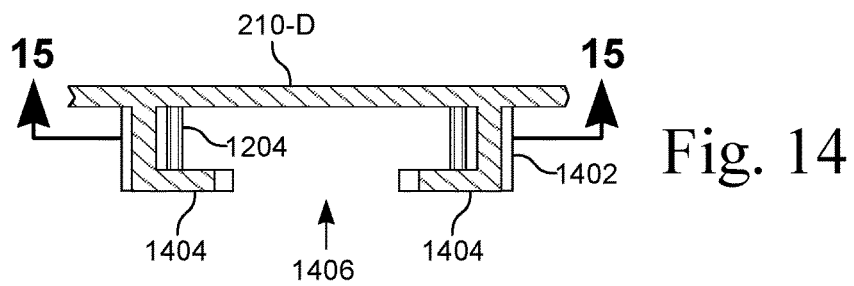
FIG. 14 is a partial cross-sectional view of a fourth embodiment of the latch.
Figure 15:
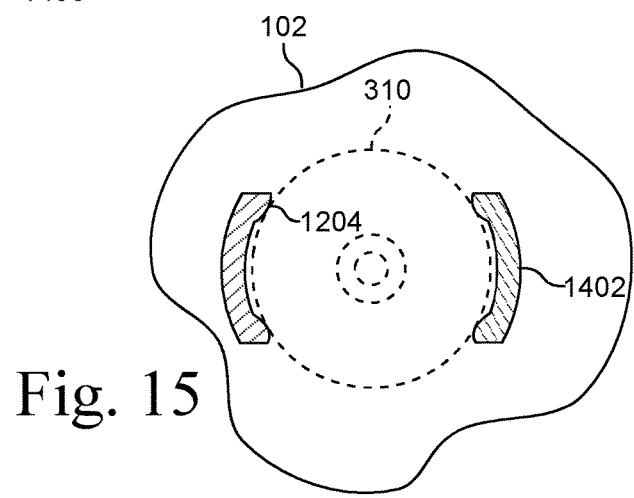
FIG. 15 is another partial cross-sectional view of the fourth embodiment of the latch with an actuator, shown in phantom, in the latch.

FIG. 13 illustrates a perspective view of a fourth embodiment of a drape support 102-D. FIG. 14 illustrates a partial cross-sectional view of a fourth embodiment of the latch 210-D. FIG. 15 illustrates another partial cross-sectional fourth of the fourth embodiment of the latch 210-D. The fourth embodiment of the drape support 102-D includes a support member 202-C and a latch 210-D. The latch 210-D is similar to the latch 210-A illustrated in FIGS. 2-5 with the addition of the protrusions 1204 and slightly different plate 1404 configuration.

The support member 202-C has a disk-shape. The support member 202-C includes a plate 1002-C and a rim 1004 that projects downward in the same direction that the latch 210-D projects from the plate 1002-C. The latch 210-D is positioned in the center of the drape support 202-C.

The illustrated embodiment of the latch 210-D has two sidewalls 1402 that are opposed and coincident with a partial cylinder. A pair of plates, or keepers, 1404 are spaced from the bottom surface of the drape support 102-D with a gap sufficient to accommodate the disk of the actuator 310. Between the plates 1404 is a gap 1406 that is dimensioned to accommodate the shaft connection to the actuator 310 when the latch 210-D moves in the direction 214 relative to the actuator 310.

The sidewalls 1402 of the latch 210-D have opposing openings with a width 306 that is slightly less than the diameter of the actuator 310 such that when the drape support 102-D is moved in the direction 214 relative to the actuator 310, the latch 210-D receives the actuator 310 and holds the actuator 310 captive within the latch 210-DC. Inside the openings 306 of the sidewalls 1402 at each inside edge is a protrusion 1204. The four protrusions 1204 are raised bumps or ridges that extend inward from the sidewalls 1402. The sidewalls 1402 are resilient such that when the latch 210-D engages the actuator 310 the sidewalls 1402 deform to allow the actuator 310 to move within the latch 210-D and be retained between the sidewalls 1402. When the actuator 310 is held captive by the sidewalls 1402, the protrusions 1204 contact points on the circumference of the actuator 310, thereby securing the actuator 310 to the sidewalls 1402 and to the drape support 102-C.

Figure 16:
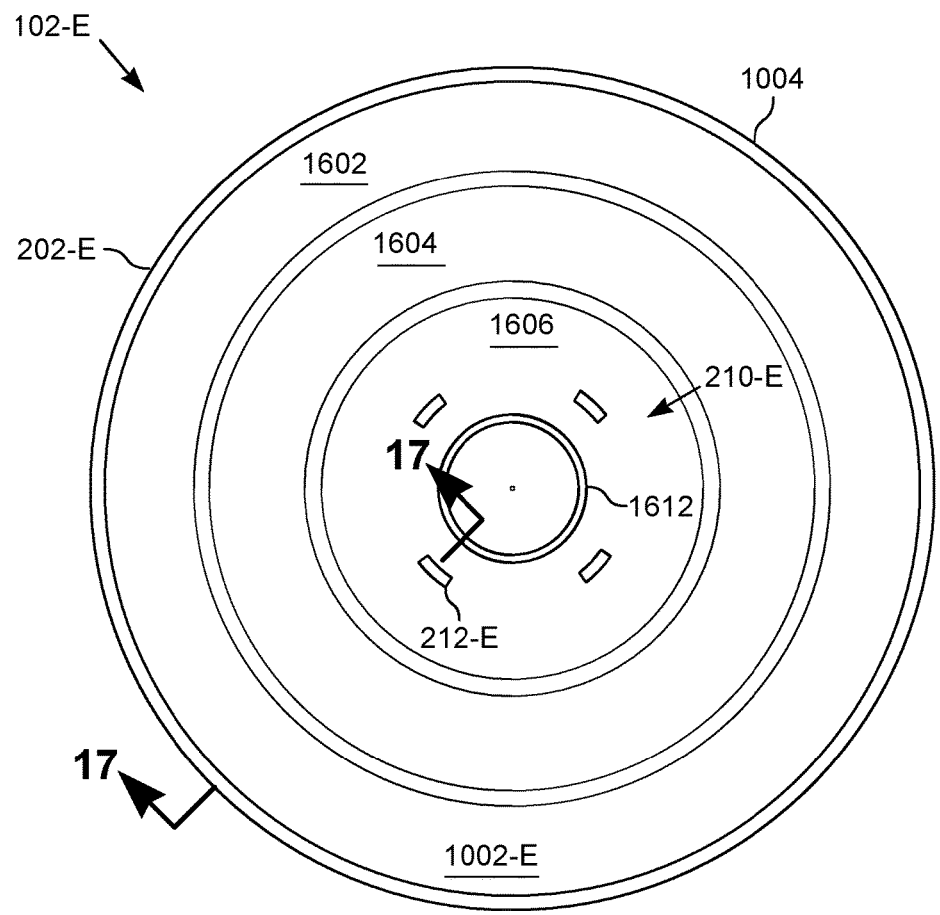
FIG. 16 is a bottom plan view of a fifth embodiment of an agitator.
Figure 17:
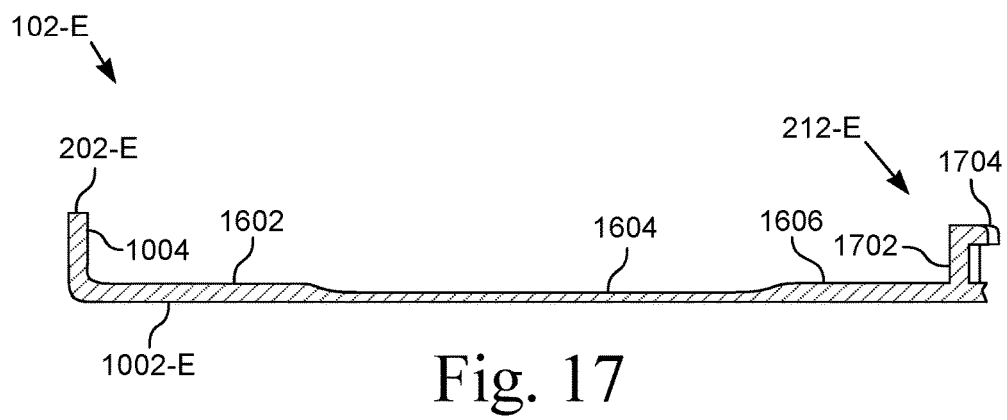
FIG. 17 is a partial cross-sectional view of the agitator of FIG. 16.

FIG. 16 illustrates a bottom plan view of a fifth embodiment of an agitator 102-E. The agitator 102-E has a support member 202-E and a latch 210-E. FIG. 17 illustrates a partial cross-sectional view of the agitator 102-E of FIG. 16. The support member 202-E includes a disk-shaped plate 1002-E and a rim 1004 at the periphery of the plate 1002-E. The plate 1002-E of the agitator 102-E has regions 1602, 1604, 1606 of varying thickness between the rim 1004 and the latch 210-E. The latch 210-E is substantially centered on the bottom of the plate 1002-E.

The plate 1002-E of the agitator 102-E is circular with a rim 1004 extending under the plate 1002-E and away from the bottom surface of the plate 1002-E. The plate 1002-E has an outer annular section 1602 adjacent the rim 1004 that has a first thickness. The plate 1002-E has a disc section 1606 that is centered in the plate 1002-E. Between the outer annular section 1602 and the disc section 1606 is an inner annular section 1604. FIG. 16 illustrates the annular sections 1602, 1604 as being circular and centered on the plate 1002-E. Other embodiments have different configurations and shapes of the various sections 1602, 1604, 1606 in order to produce a desired flex and bending motion of the agitator 102-E when it is in operation.

The outer annular section 1602 has a first thickness. The inner annular section 1604 has a second thickness. The disc section 1606 has a third thickness. In the illustrated embodiment the first and third thicknesses are equal in thickness with the second thickness approximately one-half the thickness of the first thickness. For example, the first and third thicknesses are 60 mils and the second thickness is 30 mils. The plate 1002-E has a region of weakness that allows the plate 1002-E to flex and bend. The region of weakness is defined by the thinner inner annular section 1604 surrounded by the thicker outer annular section 1602 and the disc section 1606. With the region of weakness the plate 1002-E flexes and bends when operated upon by the actuator 310 and agitating a load of slush contained in the drape 104.

The latch 210-A includes spaced apart prongs 212-E that extend away from the bottom of the drape support 102-E. The prongs 212-E each have a side member 1702 and a ledge 1704. The side members 1702 of the prongs 212-E are flexible and resilient so as to receive the actuator 310 axially. That is, the agitator 102-E and latch 210-E are pressed down onto the actuator 310 such that the prongs 212-E spread apart to receive the actuator 310 and then return to position to grasp the actuator 310 between the prongs 212-E. The plate 1002-E has a raised section 1612 that contacts the outer surface of the actuator 310, that is the surface proximate the agitator 102-E. FIG. 17 illustrates a circular raised rim or ridge 1612, although other shapes can be used. Each ledge 1704 on the prongs 212-E engages the opposite surface of the actuator 310, thereby capturing the actuator 310 between the raised section 1612 and the ledges 1704. In various embodiments the prongs 212-E include protrusions 1204 that bias the actuator 310 against the opposing sidewalls 1702 and/or against the bottom surface of the plate 1002-E or the raised section 1612.

The drape assembly 100 and drape support or agitator 102 include various functions. The function of supporting the drape 104 is implemented, in one embodiment, by support member 202, which is positioned under the drape 104 when the drape 104 is disposed in the basin 106. In one such embodiment the function of supporting the drape 104 is implemented by the paddles 204. In other such embodiments the function of supporting the drape 104 is implemented by the disk-like support member 202-C, 202-E, which is positioned under the drape 104 when the drape 104 is disposed in the basin 106.

The agitator 102 includes various functions. The function of introducing random motions during operation is implemented, in various embodiments by a region or area of weakness in the support member 202. In one such embodiment the function of introducing random motions during operation is implemented by the paddle configuration, such as illustrated in FIGS. 2 to 4. In another such embodiment the function of introducing random motions during operation is implemented by adding holes 902 that weaken the neck 208 of the support member 202-B, such as illustrated in FIG. 9. In yet another such embodiment the function of introducing random motions during operation is implemented with the regions of varying thickness in the plate 1002-E, such as illustrated in FIGS. 16 and 17. Random motions are defined as movements of the support member 202 resulting from the support member 202 flexing and bending when in operation to agitate slush in a slush machine 110. Those movements vary based on the consistency of the slush solution supported by the plate 1002-E.

The function of securing the agitator 102 to the actuator 310 of the slush machine 110 is implemented, in one embodiment, by a latch 210. In one such embodiment, the latch 210-A includes a pair of opposed prongs 212 that extend away from the bottom of the agitator 102-A. In a second such embodiment, the latch 210-B includes a sidewall 702 and a plate or keeper 704 such as illustrated in FIGS. 6 to 9. In a third such embodiment, the latch 210-C includes a sidewall 1102 that is a partial cylinder and a plate, or keeper, 1104 that is spaced from the bottom surface of the drape support 102-C with a gap sufficient to accommodate the disk of the actuator 310, such as illustrated in FIGS. 10 to 12. In a fourth such embodiment, the latch 210-D includes two sidewalls 1402 that are opposed and coincident with a partial cylinder and further includes a pair of plates, or keepers, 1404 that are spaced from the bottom surface of the drape support 102-D with a gap sufficient to accommodate the disk of the actuator 310, such as illustrated in FIGS. 13-15. In a fifth such embodiment, the latch 210-E includes a plurality of spaced apart prongs 212-E that extend away from the bottom of the drape support 102-E, such as illustrated in FIGS. 16 and 17.

From the foregoing description, it will be recognized by those skilled in the art that a drape assembly 100 has been provided. The drape assembly 100 includes a drape 104 and a drape support 102. The drape is sterile on one side and on the other side has the drape support 102. The drape support 102 has a support member 202 and a latch 210. The support member 202 includes several embodiments. One embodiment of a support member 202-A, 202-B includes multiple paddles 204 extending away from the latch 210. Other embodiments of a support member 202-C, 202-E includes a disk with a plate 1002-C, 1002-E and a rim 1004.

From the foregoing description, it will also be recognized by those skilled in the art that an agitator 102 with improved slush production has been provided. The agitator 102 includes a support member 202 and a latch 210. In various embodiments the support member 202 is configured to flex and bend, which contributes to producing random motions to the slush mixture in the basin 106 of the slush machine 110. In this way ice is prevented from forming on the sidewalls of the basin 106. In various embodiments the support member 202-A has a plurality of paddles 204 extending outward from the latch 210. In another embodiment the support member 202-E has a plate 1002-E that is disc-shaped with a region of reduced thickness 1604 in the plate 1002-E. In another embodiment of the support member 202-C, the member 202-C has a plate 1002-C that is disc-shaped and rigid.

In various embodiments the latch 210 is configured to secure the agitator 102 to an actuator 310 of the slush machine 110. Various embodiments of the latch 210-A, 210-E include a plurality of prongs 212-A, 212-E that engage the actuator 310. A first embodiment of a latch 210-A includes a pair of opposed prongs 212-A that each have a sidewall 302 and a tab 304. In this embodiment the prongs 212-A are configured to engage the side and bottom of the actuator 310 after it is slid laterally between the pair of prongs 212-A. A fifth embodiment of a latch 210-E includes a plurality of prongs 212-E that each have a sidewall 1702 and a ledge 1704. In this embodiment the prongs 212-E are configured to engage the side and bottom of the actuator 310 after it is slid axially between the plurality of prongs 212-E.

Other embodiments of the latch 210-B, 210-C, 210-D include one or more sidewalls 702, 1102, 1402 that are configured to engage the side and bottom of the actuator 310 after it is slid laterally into the latch 210-B, 210-C, 210-D. For example, a second embodiment of a latch 201-B includes a partial cylinder with a sidewall 702 and a plate 704 that encloses one end of the partial cylinder. A third embodiment of a latch 210-C includes a partial cylinder with a sidewall 1102 that has protrusions 1204 and with a plate 1104 extending from the sidewall 1102. The plate 704 has an opening to accommodate the shaft of the actuator 310. A fourth embodiment of a latch 210-D includes a pair of sidewalls 1402 forming a partial cylinder and a plate 1404 extending from each sidewall 1402. The inside edges of the sidewalls 1402 have protrusions 1204 extending inward. The plates 1404 have a slot accommodating the shaft of the actuator 310.

In various embodiments of the drape support, or agitator, 102, any of the embodiments of the support member 202-A, 202-B, 202-C, 202-E can be combined with any of the embodiments of the latch 210-A, 210-B, 210-C, 210-D, 210-E.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for agitating a slush solution contained in a slush machine, the slush machine having an actuator that is disc-shaped, the actuator moving with a reciprocating motion, said apparatus comprising:
   a support member having a first surface configured to attach to a drape, said support member having a second surface opposite said first surface, said support member having a disc-shape with an outer annular region, an inner annular region, and a central region, said inner annular region disposed between said outer annular region and said central region, said inner annular region having a first thickness that is thinner than a second thickness of said central region and said first thickness of said inner annular region being thinner than a third thickness of said outer annular region whereby said inner annular region defines a region of weakness allowing said support member to flex and bend when the slush solution is being agitated; and
   a latch configured to engage the actuator, and said latch substantially centered on said second surface of said support member and protruding from said central region with said inner annular region outboard of said latch.

2. The apparatus of claim 1 wherein said first thickness is less than or equal to one-half of said second thickness.

3. The apparatus of claim 1 wherein said latch includes a plurality of prongs each having a sidewall and a ledge, each of said ledges defining a gap sufficient to capture said actuator when said actuator engages said latch.

4. The apparatus of claim 3 wherein said sidewalls and said ledges are configured to engage said actuator when said actuator is moved into said latch in a direction parallel to said second surface of said support member.

5. The apparatus of claim 3 wherein said sidewalls and said ledges are configured to engage said actuator when said actuator is moved into said latch in a direction perpendicular to said second surface of said support member.

6. The apparatus of claim 1 further including a drape attached to said first surface of said support member, and said drape having a size and configuration suitable to contain the slush solution in the slush machine.

7. An apparatus for agitating a slush solution, said apparatus comprising:
   a support member having a first surface configured to attach to a drape, said support member having a second surface opposite said first surface, said support member being flexible such that said support member flexes and bends when the slush solution is being agitated; and
   a latch configured to releasably engage an actuator that is disc-shaped.

8. The apparatus of claim 7 wherein said support member has a disc-shape with said latch substantially centered in said support member.

9. The apparatus of claim 7 wherein said support member has a disc-shape with said latch substantially centered in said support member, said support member having an annular region with a first thickness that is thinner than a second thickness of an adjacent region.

10. The apparatus of claim 9 wherein said first thickness is less than or equal to one-half of said second thickness.

11. The apparatus of claim 7 wherein said support member has a plurality of paddles extending outward from said latch, each one of said plurality of paddles having a head and a neck.

12. The apparatus of claim 11 wherein each of said necks is narrower than a corresponding one of said heads whereby each one of said plurality of paddles flexes and bends when the slush solution is being agitated.

13. The apparatus of claim 11 wherein each of said necks includes a region of weakness sufficient to allow said plurality of paddles to flex and bend.

14. The apparatus of claim 11 wherein each of said necks includes a plurality of openings with a size and number sufficient to allow said plurality of paddles to flex and bend.

15. An apparatus for agitating a slush solution contained in a slush machine, the slush machine having an actuator that is disc-shaped, the actuator moving with an oscillating motion, said apparatus comprising:
   a support member having a first surface configured to attach to a drape, said support member having a second surface opposite said first surface, said support member including means for introducing random motions when the slush solution is being agitated; and
   a means for securing said support member to the actuator of the slush machine.

16. The apparatus of claim 15 wherein said means for introducing random motions includes a plurality of paddles extending from a center of said support member.

17. The apparatus of claim 15 wherein said means for introducing random motions includes a region of weakness in said support member.

18. The apparatus of claim 17 wherein said region of weakness in said support member is defined by a region having a first thickness that is less than a second thickness of an adjacent region.

19. The apparatus of claim 15 wherein said means for securing said support member includes a plurality of prongs that each include a sidewall wherein the actuator is received between said plurality of sidewalls and the actuator is received between said second surface and a member protruding from a distal end of each one of said plurality of sidewalls.

20. The apparatus of claim 15 wherein said means for securing said support member includes a partial cylinder extending from said second surface of said support member, said partial cylinder configured to receive the actuator when the actuator moves relative to said support member in a direction parallel to a plane defined by said bottom surface of said support member.

* * * * *